(12) United States Patent
Theriot et al.

(10) Patent No.: US 10,123,899 B1
(45) Date of Patent: Nov. 13, 2018

(54) ORTHOPEDIC DEVICE AND METHOD OF USE

(71) Applicants: Trevor James Theriot, Costa Mesa, CA (US); John Nigel Lasso, Laguna Hills, CA (US)

(72) Inventors: Trevor James Theriot, Costa Mesa, CA (US); John Nigel Lasso, Laguna Hills, CA (US)

(*) Notice: Subject to any disclaimer, the term of this patent is extended or adjusted under 35 U.S.C. 154(b) by 368 days.

(21) Appl. No.: 15/093,870

(22) Filed: Apr. 8, 2016

(51) Int. Cl.
*A61F 5/37* (2006.01)
*A61F 5/01* (2006.01)
*A61F 5/058* (2006.01)

(52) U.S. Cl.
CPC .......... *A61F 5/3753* (2013.01); *A61F 5/0118* (2013.01); *A61F 5/05866* (2013.01); *A61F 5/3738* (2013.01)

(58) Field of Classification Search
CPC .... A61F 5/3738; A61F 5/3746; A61F 5/3753; A61F 5/3723; A61F 5/0118; A61F 5/05808
USPC ...................................... 602/19–20
See application file for complete search history.

(56) References Cited

U.S. PATENT DOCUMENTS

| 2,661,000 A | * | 12/1953 | Gazeley | A61F 5/3753 602/16 |
| 4,836,195 A | | 6/1989 | Berrehail | |
| 5,033,461 A | * | 7/1991 | Young | A61F 5/3753 602/16 |
| 5,385,536 A | * | 1/1995 | Burkhead | A61F 5/3753 2/45 |
| 2014/0221888 A1 | | 8/2014 | Benenati | |
| 2016/0278963 A1 | * | 9/2016 | Webster | A61F 5/026 |

* cited by examiner

Primary Examiner — Ophelia A Hawthorne
(74) Attorney, Agent, or Firm — Ted Masters

(57) ABSTRACT

An orthopedic device can be worn by a person having a waist, a shoulder, and an arm including an upper arm and a forearm. The orthopedic device holds the arm of the person in an abducted immobilized position to promote healing. The orthopedic device includes a sling which is shaped and dimensioned to receive the arm of the person, the sling includes a shoulder strap which is positionable over the shoulder of the person. The orthopedic device also includes a belt which is shaped and dimensioned to encircle the waist of the person. An arm support for supporting the person's arm is removably connectable to the belt. The belt includes an arm support connector to which the arm support is removably and fixedly connected so that the arm support projects upwardly from the belt. The arm support is positionable to extend different heights above the belt. The sling is connectable to the arm support so that the arm of the person is abducted.

3 Claims, 5 Drawing Sheets

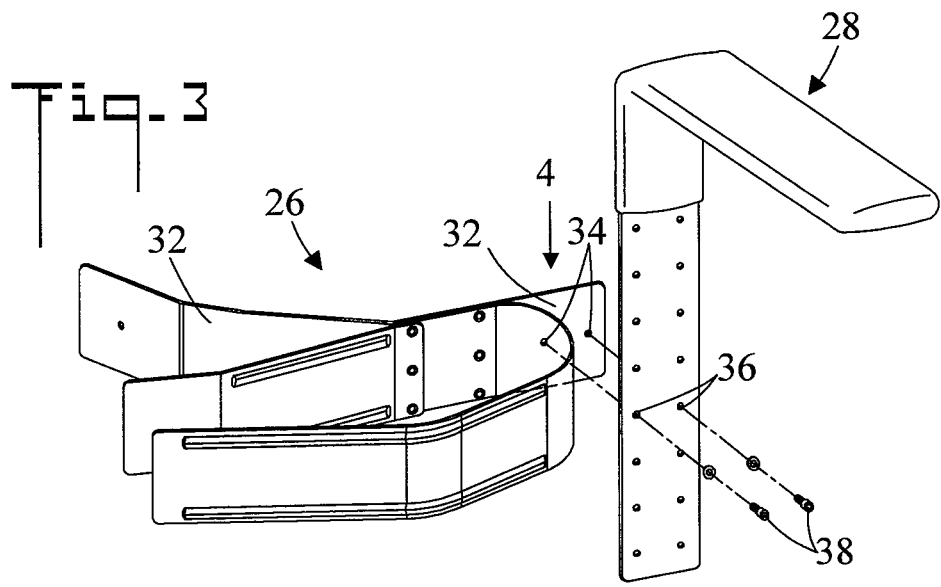
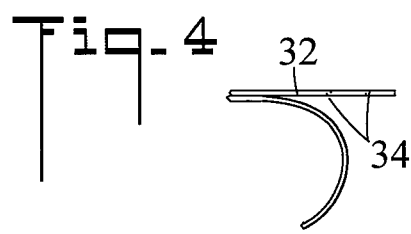
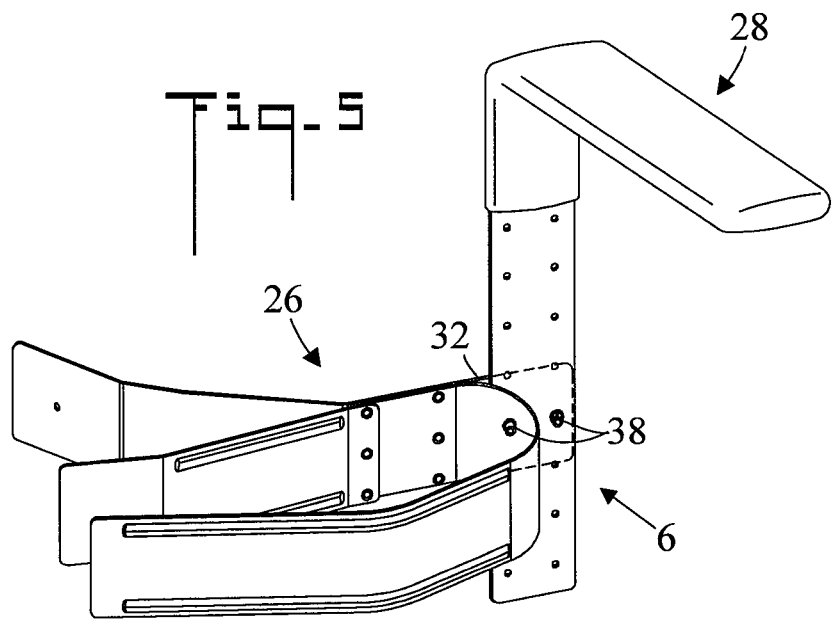

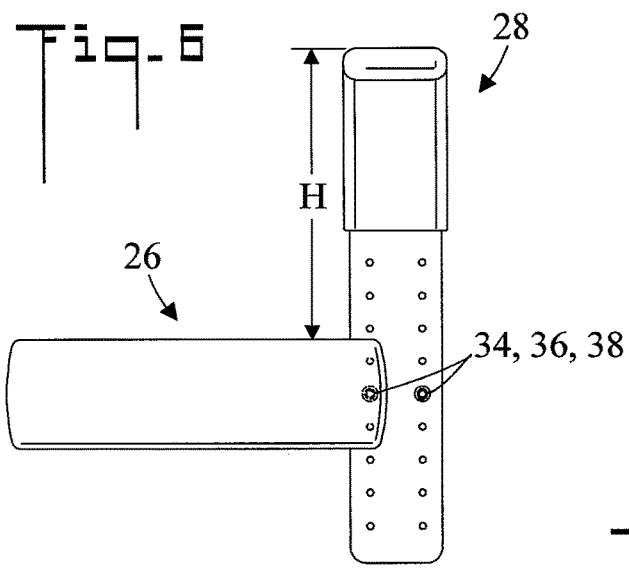
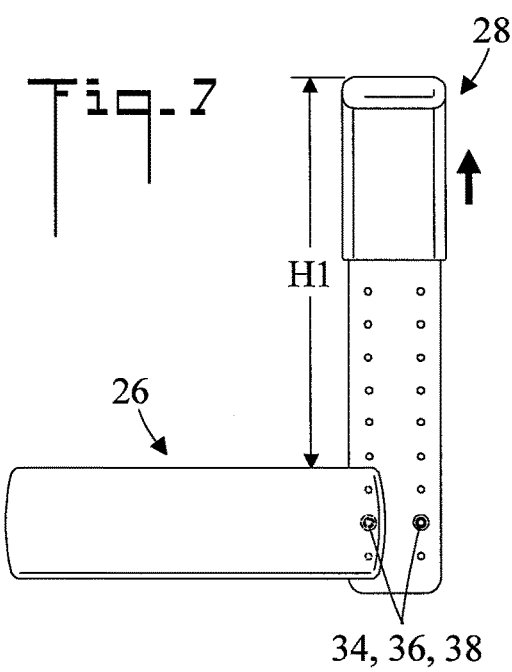
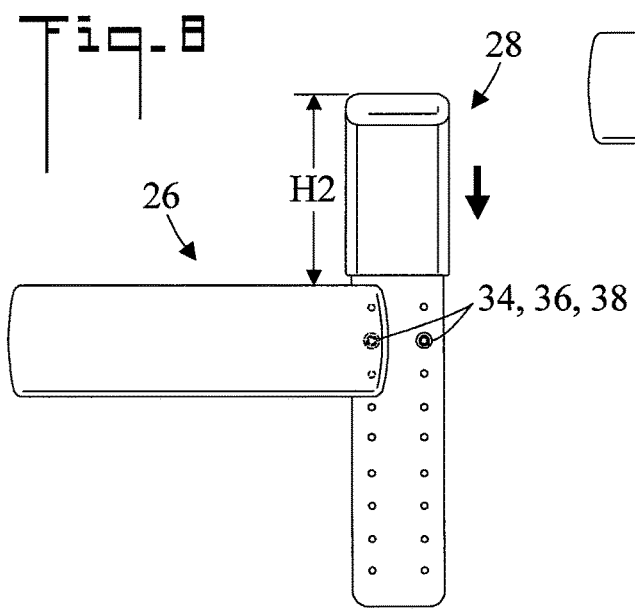

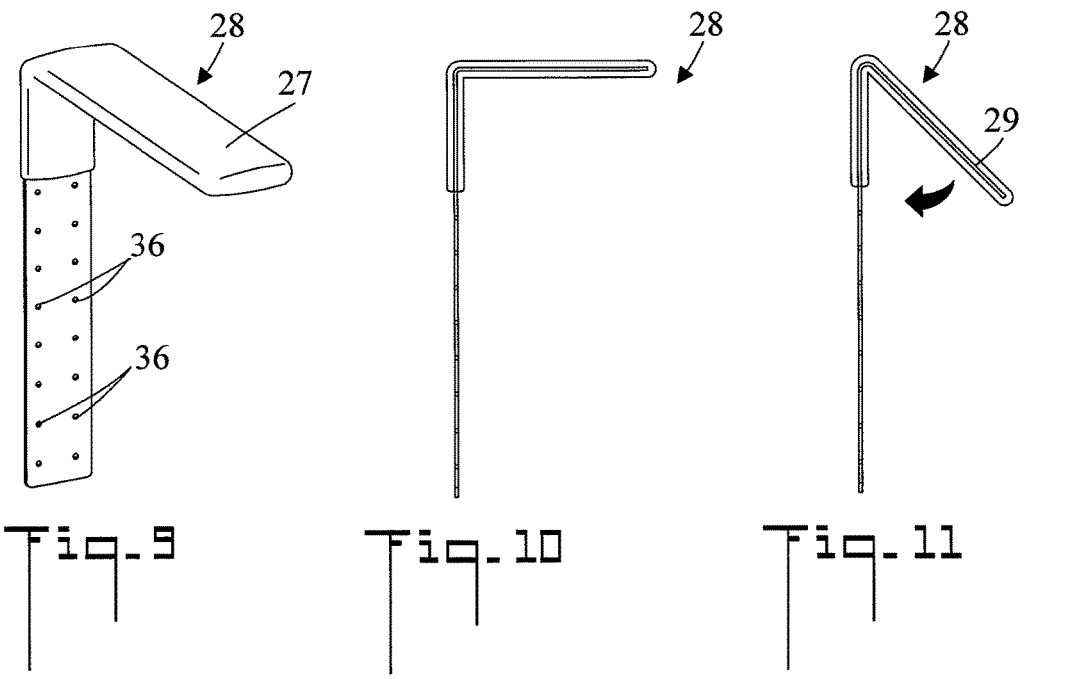
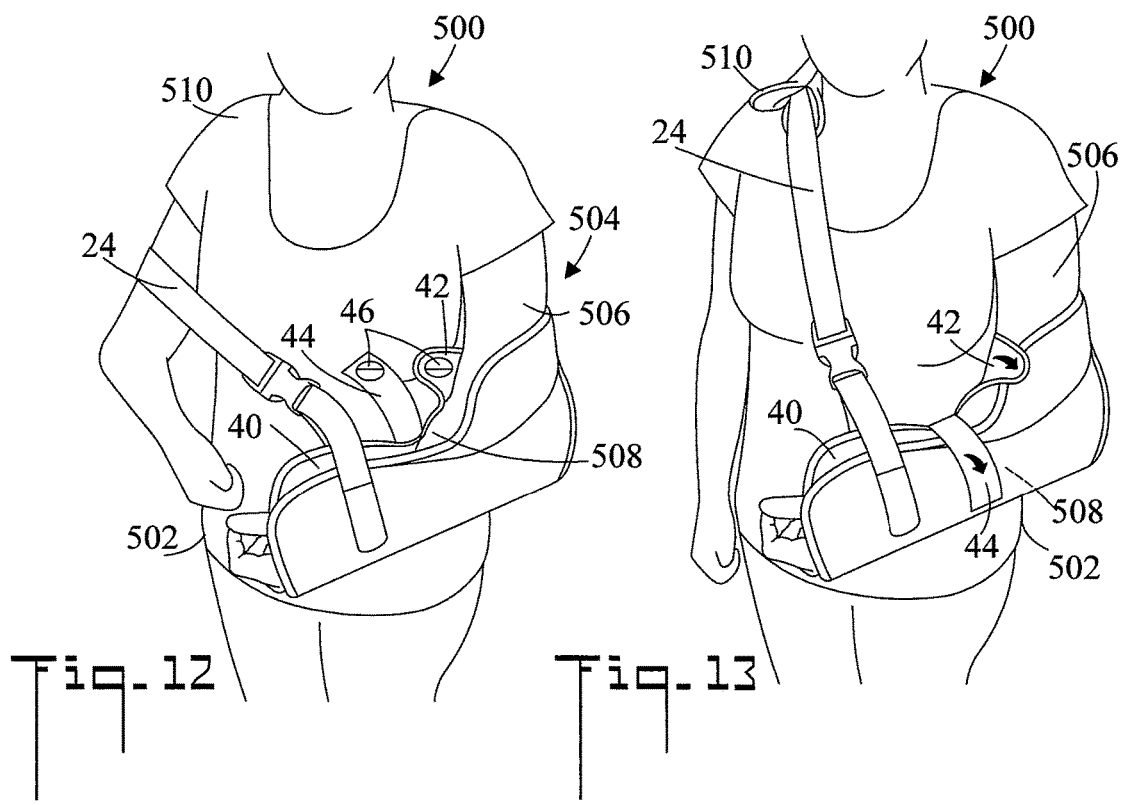

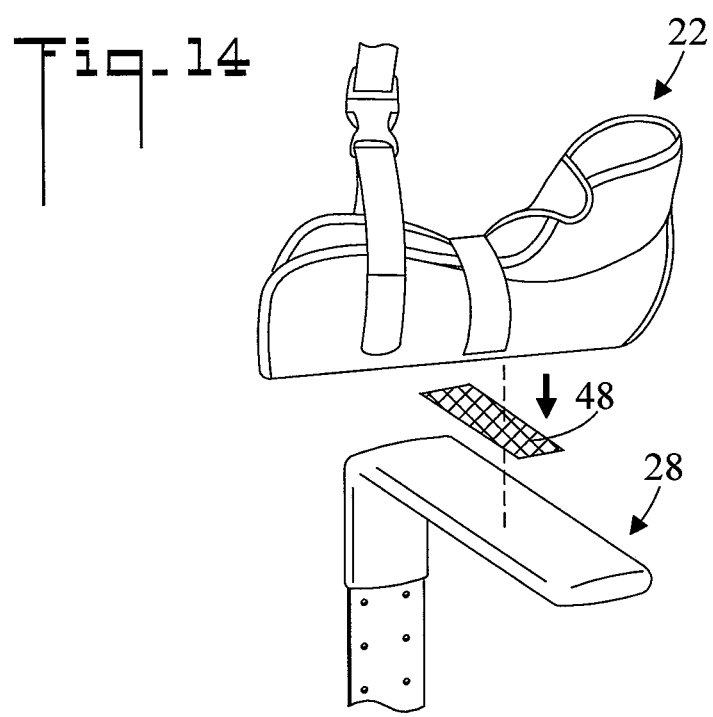

US 10,123,899 B1

ORTHOPEDIC DEVICE AND METHOD OF USE

CROSS REFERENCE TO RELATED APPLICATION

None

TECHNICAL FIELD

The present invention pertains generally to the field of medicine, and more particularly to an orthopedic device which holds the arm of a person in a desired position to promote healing after an injury or surgery.

BACKGROUND OF THE INVENTION

Orthopedic devices such as braces and slings are well know in the art. These devices are temporarily used to support and immobilize a part of the body after an injury or surgery. For example in the case of shoulder surgery, it is advantageous to restrict arm movement during the healing process. This often includes keeping the arm in an outward and upward "abducted" position away from the body.

BRIEF SUMMARY OF THE INVENTION

The present invention is directed to an orthopedic device which holds the arm of a person in an immobilized abducted position to promote healing. The orthopedic device includes an arm support which can be adjusted to hold the arm at a desired height.

In accordance with an embodiment, an orthopedic device is wearable by a person having a waist, an arm which includes an upper arm and a forearm, and a shoulder. The orthopedic device includes a sling which is shaped and dimensioned to receive the arm of the person, the sling includes a shoulder strap which is positionable over the shoulder of the person. A belt is shaped and dimensioned to encircle the waist of the person. An arm support is provided for supporting the arm of the person. The belt includes an arm support connector. The arm support is removably connectable to the arm support connector so that the arm support can be connected to the belt and upwardly project therefrom. The arm support is positionable to extend different heights above the belt. The sling is connectable to the arm support so that the arm of the person is abducted.

In accordance with another embodiment, the arm support includes a plurality of height adjustment stations which permit the arm support to be adjusted to different heights above the belt. A selected one of the plurality of height adjustment stations is connected to the arm support connector to effect a desired arm support height above the belt.

In accordance with another embodiment, the arm support connector includes two holes. The height adjustment stations each include two adjustment holes. Two connectors are removable received by the two holes and the two adjustment holes and fixedly connect the arm support to the belt.

In accordance with another embodiment, the belt includes a malleable strip. The arm support connector is connected to the malleable strip.

In accordance with another embodiment, the arm support is fabricated from a malleable material.

In accordance with another embodiment, a sling connector connects the sling to the arm support.

In accordance with another embodiment, the sling connector includes a hook and loop fastener.

In accordance with another embodiment, the sling includes a pocket which is shaped and dimension to receive the arm of the person. The sling includes first and second straps which hold the arm of the person in the pocket.

In accordance with another embodiment, the first strap is disposed so that when it is connected it abuts the upper arm of the person.

Other embodiments, in addition to the embodiments enumerated above, will become apparent from the following detailed description, taken in conjunction with the accompanying drawings, which illustrate, by way of example, the principles of the orthopedic device and method of use.

BRIEF DESCRIPTION OF THE DRAWINGS

FIG. 3 is an exploded perspective view of the belt with padding removed and the arm support;

FIG. 4 is a fragmented view in direction 4 of FIG. 3;

FIG. 5 is a perspective view with the arm support connected to the belt;

FIG. 6 is a front elevation view of the arm support at a first height above the belt;

FIG. 7 is a front elevation view of the arm support at a second higher height above the belt;

FIG. 8 is a front elevation view of the arm support at a third lower height above the belt;

FIG. 9 is a perspective view of the arm support;

FIG. 10 is a side elevation view of the arm support;

FIG. 11 is a side elevation view of an upper portion of the arm support bent to a different angle;

FIG. 12 is a perspective view of an arm of a person placed in a sling;

FIG. 13 is a perspective view of the arm in the sling with the sling connected and with the shoulder strap of the sling positioned over the shoulder of the person; and, FIG. 14 is an exploded perspective view of the sling being connected to the arm support.

DETAILED DESCRIPTION OF THE INVENTION

Figure 1:
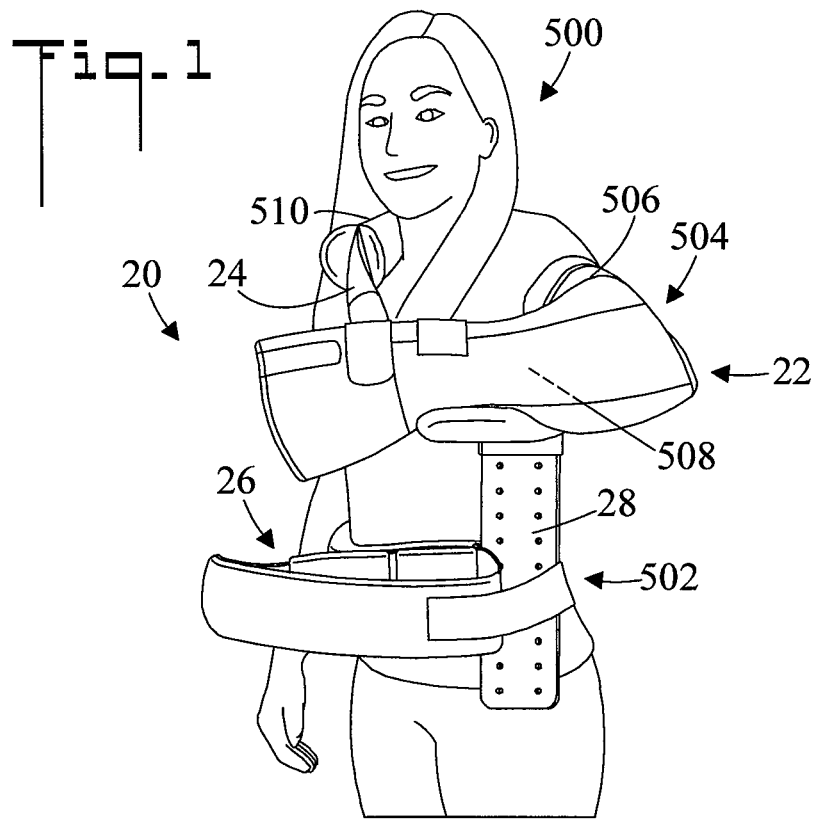
FIG. 1 is a reduced perspective view of an orthopedic device being worn by a person.

Referring initially to FIG. 1, there is illustrated an orthopedic device 20 which is wearable by a person 500 having a waist 502, an arm 504 which includes an upper arm 506 and a forearm 508, and a shoulder 510 (also refer to FIGS. 12 and 13). Waist 502 is the area below the ribs and above the hips, upper arm 506 is the area between the elbow and the shoulder, and forearm 508 is the area between the elbow and the hand.

Orthopedic device 20 includes a sling 22 which is shaped and dimensioned to receive the arm 504 of the person 500. Sling 22 typically receives forearm 508 and the lower portion of upper arm 506. Sling 22 includes a shoulder strap 24 which is positionable over the shoulder 510 of the person 500 to support sling 22.

Orthopedic device 20 further includes a belt 26 (refer also to FIGS. 2-4) which is shaped and dimensioned to encircle the waist 502 of person 500. Orthopedic device 20 also includes an arm support 28 for supporting the arm 504 of the person 500. Arm support 28 is removably connectable to belt 26 (refer also to FIG. 3), and holds the arm 504 of the person 500 in an elevated abducted position as is shown in FIG. 1. When connected to belt 26, arm support 28 upwardly projects from belt 26 in an upright orientation generally perpendicular to belt 26, and arm support 28 is positionable to extend different heights above belt 26 (also refer to FIGS. 6-8 and the associated discussions). Sling 22 is removably connectable to arm support 28 so that the arm 504 of the person 500 is abducted.

Figure 2:
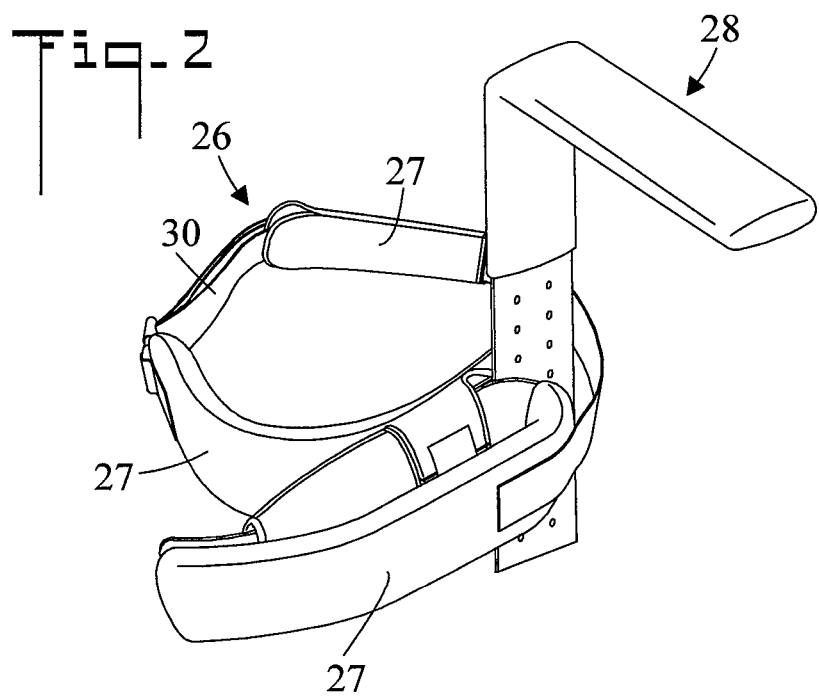
FIG. 2 is a perspective view of a belt with a connected arm support.

FIG. 2 is a perspective view of belt 26 with connected arm support 28. It is noted that belt 26 contains cloth covered padding 27 which provides cushioning for the waist 502 of the person 500 (refer to FIG. 1). Also, belt 26 includes a waist adjustment 30.

FIG. 3 is an exploded perspective view of belt 26 with padding 27 removed (for clarity) and arm support 28, and FIG. 5 is a perspective view with arm support 28 connected to belt 26. In an embodiment, belt 26 includes a malleable strip 32 which is shapable to fit the waist 502 of the person 500. That is, malleable strip 32 may be bent to conform to the curvature of the waist 502 of a particular person 500, and will remain in the bent shape. A malleable metal such as aluminum can be utilized for this purpose. Belt 26 includes an arm support connector 34 wherein arm support 28 can be removably connected to arm support connector 34 so that arm support 28 can be connected to belt 26 and upwardly project therefrom. In the shown embodiment, arm support connector 34 is connected to (is a part of) malleable strip 32.

Still referring to FIG. 3, arm support 28 includes a plurality of height adjustment stations 36 which permit arm support 28 to be adjusted to different heights above belt 26 (refer also to FIGS. 6-8 and the associated discussions). A selected one of the plurality of the height adjustment stations 36 is connected to arm support connector 34 to effect a desired arm support height above belt 26). In the shown embodiment, arm support connector 34 includes two holes in malleable strip 32. The height adjustment stations 36 each include two adjustment holes. Two connectors 38 are removable received by two holes 34 and two adjustment holes 36. In the shown embodiment, two holes 34 are threaded, adjustment holes 36 include two through holes, and connectors 38 are screws which go though adjustment holes 36 and engage threaded holes 34 to fixedly connect arm support 28 to belt 26. Fixedly connected means that arm support 28 and malleable strip 32 are locked together as a single unit, and must be disconnected in order to be separated.

FIG. 4 is a view in direction 4 of FIG. 3, showing a top plan view of malleable strip 32 with threaded holes 34 for connecting arm support 28.

FIG. 6 is a front elevation view (in direction 6 of FIG. 5) of the arm support 28 at a first adjusted height H above belt 26. FIG. 7 is a front elevation view of arm support 28 at a second higher adjusted height H1 above belt 26. FIG. 8 is a front elevation view of arm support 28 at a third lower adjusted height H2 above belt 26. Connectors 38, adjustment holes 36, and threaded holes 34 are utilized to connect arm support 28 to belt 26 at different heights above belt 26 as an orthopedic situation may dictate.

FIGS. 9 and 10 are perspective and side elevation views respectively of arm support 28 showing the plurality of pairs of adjustment holes 36, and FIG. 11 is a side elevation view of an upper portion 29 of arm support 28 bent to a different angle (45° as opposed to the 90° of FIG. 10). In an embodiment, arm support 28 is fabrication from a malleable material (such as malleable strip 32 above) so that it can be bent to accommodate different abduction needs. Upper portion 29 of arm support 28 includes cloth covered padding 27.

FIG. 12 is a perspective view of the arm 504 of the person 500 placed in sling 22, and FIG. 13 is a perspective view of the arm 504 of the person 500 in sling 22 with sling 22 connected and with shoulder strap 24 of sling 22 positioned over the shoulder 510 of the person 500. Sling 22 includes a pocket 40 which is shaped and dimension to receive the arm 504 of the person 500 (also refer to FIG. 14). Sling 22 also includes first 42 and second 44 straps which hold the arm 504 of the person 500 in pocket 40. First strap 42 is disposed so that when it is connected (refer to 13) it abuts the upper arm 506 (biceps area) of the person 500. In the shown embodiment the connection of first 42 and second 44 straps includes the straps having one of hook-and-loop material 46, and the body of sling 22 having the other of hook-and-loop material.

FIG. 14 is an exploded perspective view of sling 22 being connected to arm support 28. A sling connector 48 is provided for connecting sling 22 to arm support 28 (also refer to FIG. 1). In the shown embodiment sling connector 48 is a double sided hook and loop fastener (hook material) which connects sling 22 to arm support 28.

In terms of use, a method for abducting the arm 504 of a person 500, the person 500 having a waist, a shoulder 510, the arm 504 including an upper arm 506 and a forearm 508, the method including: (refer to FIGS. 1-14)

(a) providing an orthopedic device 20 including:
  a sling 22 which is shaped and dimensioned to receive the arm 504 of the person 500, the sling 22 including a shoulder strap 24 which is positionable over the shoulder 510 of the person 500;
  a belt 26 which is shaped and dimensioned to encircle the waist 502 of the person 500;
  an arm support 28 for supporting the arm 504 of the person 500;
  the belt 28 including an arm support connector 34;
  an arm support 28 is removably connectable to the arm support connector 34 so that the arm support 28 can be connected to the belt 26 and upwardly project therefrom;
  the arm support 28 positionable to extend different heights above the belt 26;
  the sling 22 connectable to the arm support 28 so that the arm 504 of the person 500 is abducted;

(b) placing the belt 26 around the waist 502 of the person 500;

(c) connecting the arm support 28 to the arm support connector 34;

(d) putting the arm 504 of the person 500 in the sling 22; and, (e) connecting the sling 22 to the arm support 28 so that the arm 504 of the person 500 is abducted.

Note: The order of the above steps can be changed. For example step (c) could be performed before step (b).

The method further including:
during (c), adjusting a height H of the arm support 28 above the belt 26 to a desired value.

The method of further including:
in (a), the arm support 28 including a plurality of height adjustment stations 36 which permit the arm support height H to be adjusted to the desired value;
in (c), connecting one of the plurality of height adjustment stations 36 to the arm support connector 34.

The method further including:
in (a), the arm support connector 34 including two holes:
in (a), the height adjustment stations 36 each including two adjustment holes;
in (a), providing two connectors 38 which are removable received by the two holes 34 and the two adjustment holes 36; and, in (c), using the two connectors 38 to fixedly connect the arm support 28 to the arm support connector 34.

The method of further including:

in (a), the belt 26 including a malleable strip 32, the arm support 28 connected to the malleable strip 32.

The method further including:

in (a), a sling connector 48 for connecting the sling 22 to the arm support 28; and, in (e) using the sling connector 48 to connect the sling 22 to the arm support 28.

The method further including:

in (a), the sling connector 48 including a hook and loop fastener.

The method further including:

in (a), the sling 22 including a pocket 40 which is shaped and dimension to receive the arm 504 of the person 500;

in (a), the sling 22 including first 42 and second 44 straps which hold the arm 504 of the person 500 in the pocket 40; and, in (d), using the first 42 and second 44 straps to hold the arm 504 in the sling 22.

The method further including:

in (a), the first strap 42 disposed so that in (d) the first strap 42 abuts the upper arm 506 of the person 500.

The embodiments of the orthopedic device and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the device and method should be construed as limiting the invention to a particular embodiment or combination of embodiments. The scope of the invention is defined by the appended claims.

We claim:

1. An orthopedic device, the device wearable by a person having a waist, an arm which includes an upper arm and a forearm, and a shoulder, the orthopedic device comprising:

a sling which is shaped and dimensioned to receive the arm of the person, said sling including a shoulder strap which is positionable over the shoulder of the person;

a belt which is shaped and dimensioned to encircle the waist of the person;

an arm support for supporting the arm of the person;

said belt including an arm support connector;

said arm support removably connectable to said arm support connector so that said arm support can be connected to said belt and upwardly project therefrom;

said arm support positionable to extend different heights above said belt;

said sling connectable to said arm support so that the arm of the person is abducted;

said arm support including a plurality of height adjustment stations which permit said arm support to be adjusted to different heights above said belt;

a selected one of said plurality of height adjustment stations being connected to said arm support connector to effect a desired arm support height above said belt;

said arm support connector including two holes;

said height adjustment stations each including two adjustment holes; and, two connectors which are removable received by said two holes and said two adjustment holes and fixedly connect said arm support to said belt.

2. An orthopedic device, the device wearable by a person having a waist, an arm which includes an upper arm and a forearm, and a shoulder, the orthopedic device comprising:

a sling which is shaped and dimensioned to receive the arm of the person, said sling including a shoulder strap which is positionable over the shoulder of the person;

a belt which is shaped and dimensioned to encircle the waist of the person;

an arm support for supporting the arm of the person;

said belt including an arm support connector;

said arm support removably connectable to said arm support connector so that said arm support can be connected to said belt and upwardly project therefrom;

said arm support positionable to extend different heights above said belt;

said sling connectable to said arm support so that the arm of the person is abducted;

said arm support including a plurality of height adjustment stations which permit said arm support to be adjusted to different heights above said belt;

a selected one of said plurality of height adjustment stations being connected to said arm support connector to effect a desired arm support height above said belt;

said arm support connector including two holes;

said height adjustment stations each including two adjustment holes;

two connectors which are removable received by said two holes and said two adjustment holes and fixedly connect said arm support to said belt;

said belt including a malleable strip;

said arm support connector connected to said malleable strip;

said arm support being fabricated from a malleable material;

a sling connector for connecting said sling to said arm support;

said sling connector including a hook and loop fastener;

said sling including a pocket which is shaped and dimension to receive the arm of the person;

said sling including first and second straps which hold the arm of the person in said pocket; and, said first strap disposed so that when it is connected to said sling it said first strap abuts the upper arm of the person.

3. A method for abducting the arm of a person, the person having a waist, a shoulder, the arm including an upper arm and a forearm, the method comprising:

(a) providing an orthopedic device including:

a sling which is shaped and dimensioned to receive the arm of the person, said sling including a shoulder strap which is positionable over the shoulder of the person;

a belt which is shaped and dimensioned to encircle the waist of the person;

an arm support for supporting the arm of the person;

said belt including an arm support connector;

an arm support removably connectable to said arm support connector so that said arm support can be connected to said belt and upwardly project therefrom;

said arm support positionable to extend different heights above said belt;

said sling connectable to said arm support so that the arm of the person is abducted;

(b) placing said belt around the waist of the person;

(c) connecting said arm support to said arm support connector;

(d) putting the arm of the person in said sling;

(e) connecting said sling to said arm support so that the arm of the person is abducted;

during (c), adjusting a height of said arm support above said belt to a desired value;

in (a), said arm support including a plurality of height adjustment stations which permit said arm support height to be adjusted to said desired value;

in (c), connecting one of said plurality of height adjustment stations to said arm support connector;

in (a), said arm support connector including two holes;

in (a), said height adjustment stations each including two adjustment holes;

in (a), providing two connectors which are removable received by said two holes and said two adjustment holes; and, in (c), using said two connectors to fixedly connect said arm support to said arm support connector.

* * * * *